US009724062B2

(12) United States Patent
Kwon et al.

(10) Patent No.: US 9,724,062 B2
(45) Date of Patent: Aug. 8, 2017

(54) X-RAY IMAGING APPARATUS AND CONTROL METHOD FOR THE SAME

(71) Applicant: SAMSUNG ELECTRONICS CO., LTD., Suwon-si (KR)

(72) Inventors: Jae-Hyun Kwon, Hwaseong-si (KR); Sungsu Kim, Yongin-si (KR); Young Hun Sung, Hwaseong-si (KR); Hyunhwa Oh, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 54 days.

(21) Appl. No.: 14/725,745

(22) Filed: May 29, 2015

(65) Prior Publication Data

US 2015/0342549 A1 Dec. 3, 2015

(30) Foreign Application Priority Data

May 29, 2014 (KR) .................. 10-2014-0065386

(51) Int. Cl.
| | |
|---|---|
| *G06K 9/00* | (2006.01) |
| *A61B 6/00* | (2006.01) |
| *G06T 5/00* | (2006.01) |
| *G06T 7/12* | (2017.01) |
| *G06T 7/155* | (2017.01) |
| *A61B 6/02* | (2006.01) |

(52) U.S. Cl.
CPC .............. *A61B 6/469* (2013.01); *A61B 6/502* (2013.01); *A61B 6/5205* (2013.01); *G06T 5/002* (2013.01); *G06T 7/12* (2017.01); *G06T 7/155* (2017.01); *A61B 6/025* (2013.01); *G06T 2207/10116* (2013.01); *G06T 2207/30068* (2013.01)

(58) Field of Classification Search
None
See application file for complete search history.

(56) References Cited

U.S. PATENT DOCUMENTS

| | | | | |
|---|---|---|---|---|
| 9,377,418 B2* | 6/2016 | Lee | ........................ | G01N 23/04 |
| 2011/0280465 A1 | 11/2011 | Wehnes et al. | | |
| 2011/0286582 A1* | 11/2011 | Iwashita | .............. | A61B 6/4266 378/146 |
| 2012/0199750 A1* | 8/2012 | Kondou | ................... | H04N 5/32 250/370.09 |
| 2013/0208956 A1* | 8/2013 | Wehnes | ................ | G06T 7/0012 382/128 |

* cited by examiner

*Primary Examiner* — Nancy Bitar
(74) *Attorney, Agent, or Firm* — Sughrue Mion, PLLC

(57) ABSTRACT

An X-ray imaging apparatus includes: an X-ray source configured to transmit X-rays; an X-ray detection assembly configured to detect the X-rays, and to convert the detected X-rays into an electrical signal; an image processor configured to generate an X-ray image based on the electrical signal; and a controller configured to process the X-ray image by changing shades of the X-ray image, and set a region of non-interest of the X-ray image based on the X-ray image and the processed X-ray image.

18 Claims, 19 Drawing Sheets

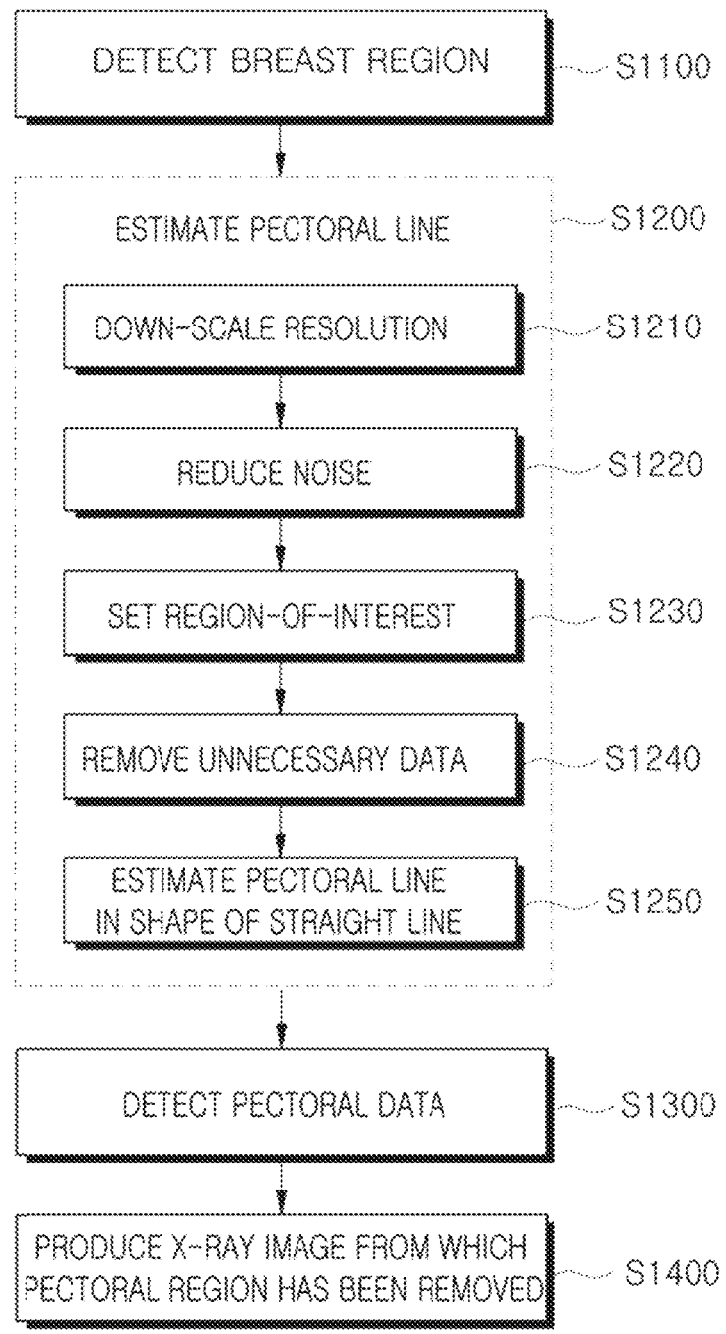

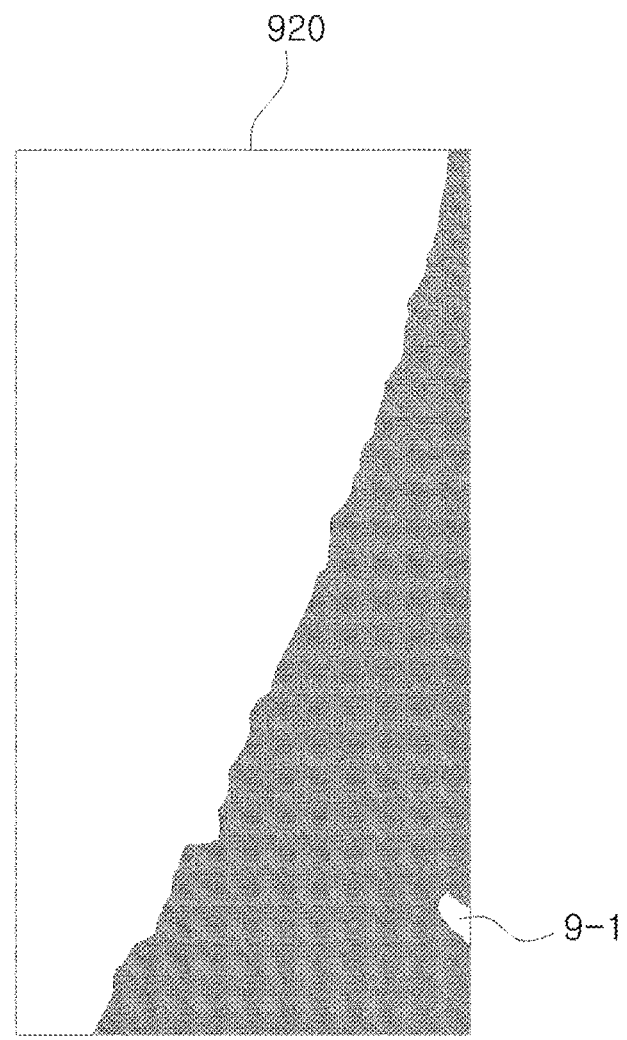

X-RAY IMAGING APPARATUS AND CONTROL METHOD FOR THE SAME

CROSS-REFERENCE TO RELATED APPLICATION

This application claims priority from Korean Patent Application No. 10-2014-0065386, filed on May 29, 2014, in the Korean Intellectual Property Office, the disclosure of which is incorporated herein in its entirety by reference.

BACKGROUND

1. Field

Apparatuses and methods consistent with exemplary embodiments relate to an X-ray imaging apparatus and a control method for the same, and more particularly, to an X-ray imaging apparatus for mammography and a control method for the same.

2. Description of the Related Art

X-rays transmitted to a specific object are passed through the object or absorbed and attenuate at a specific rate in the object, according to the internal tissues or structure of the object, or physical properties (for example, density) of materials included in the object. An X-ray imaging apparatus acquires images about the internal tissues, structure, or materials of a specific object using the properties of X-rays.

In detail, the X-ray imaging apparatus transmits X-rays to an object, detects X-rays passed through or around the object, and produces X-ray images about the internal structure, tissues, or materials of the object based on the detected X-rays. Since the X-ray imaging apparatus can show the internal structure or tissues of an object as images, the X-ray imaging apparatus is widely used to detect abnormal tissues such as lesions inside a human body at hospitals, to identify the inside structures of objects or components in industrial fields, or to scan baggage at airports.

The X-ray imaging apparatus includes radiography, computed tomography (CT), mammography, and digital breast tomosynthesis.

SUMMARY

One or more exemplary embodiments provide an X-ray imaging apparatus of generating an X-ray image from which a region of non-interest has been removed, and a control method of the X-ray imaging apparatus.

Additional aspects of the disclosure will be set forth in part in the description which follows and, in part, will be obvious from the description, or may be learned by practice of the exemplary embodiments.

In accordance with an aspect of an exemplary embodiment, an X-ray imaging apparatus includes: an X-ray source configured to irradiate X-rays; an X-ray detection assembly configured to detect the X-rays, and to convert the detected X-rays into an electrical signal; an image processor configured to read out the electrical signal, and to produce an X-ray image; and a controller configured to change shades of the X-ray image, and to set a region of non-interest of the X-ray image.

The controller may set the region of non-interest using a gradation mask.

The region of non-interest may be a pectoral region.

The controller may multiply the X-ray image by a shading mask with a pattern in which intensity is reduced from a predetermined region.

The controller may perform binary imaging on the X-ray image with the changed shades based on a threshold value to set a higher intensity region of the X-ray image to the region of non-interest, and the threshold value may be an intensity value of a position with a maximum gradient of the X-ray image.

The image processor may create an image histogram of the X-ray image, and the controller may perform binary imaging on the X-ray image based on the image histogram, and calculate gradients of the X-ray image to estimate a boundary of the region of non-interest.

The controller may set a region of interest such that a ratio of a mean value of intensity values of one or more pixels having intensity values that are smaller than a predetermined threshold value and a mean value of intensity values of one or more pixels having intensity values that are equal to or greater than the threshold value and that are equal to or smaller than a maximum intensity value becomes a predetermined ratio, and the controller may perform the binary imaging on the X-ray image, by setting one or more pixels having intensity values that are equal to or smaller than the threshold value, to a lower intensity region, and setting one or more pixels having intensity values that are equal to or greater than the threshold value and that are equal to or smaller than the maximum intensity value, to a higher intensity region.

The controller may estimate a boundary in a shape of a straight line by using a mean value of the gradients of the X-ray image as a slope.

The controller may estimate a boundary in a shape of a straight line at a position with a maximum gradient in the X-ray image.

The controller may remove unnecessary data from the binary-imaged X-ray image.

The controller may set a region in which a region of non-interest estimated based on gradients of the binary-imaged X-ray image overlaps an interference object image acquired by changing the shades of the X-ray image, to a final region of non-interest.

In accordance with an aspect of an exemplary embodiment, a control method of an X-ray imaging apparatus includes: acquiring an X-ray image; setting a region of non-interest by changing shades of the X-ray image; and removing the region of non-interest from the acquired X-ray image.

The setting of the interference object image may include setting the region of non-interest using a gradation mask.

The setting of the region of non-interest may include multiplying the X-ray image by a shading mask with a pattern in which intensity is reduced from a predetermined region.

The setting of the region of non-interest may further include performing binary imaging on the X-ray image with the changed shades based on a threshold value to set a higher intensity region of the X-ray image to the region of non-interest, wherein the threshold value may be an intensity value of a position with a maximum gradient of the X-ray image.

The setting of the region of non-interest may include: performing binary imaging on the X-ray image acquired based on an image histogram; calculating gradients of the binary-imaged X-ray image; and estimating a boundary of the region of non-interest using the gradients of the X-ray image.

The performing of the binary imaging on the X-ray image may include: setting a region of interest such that a ratio of a mean value of intensity values of one or more pixels having intensity values that are smaller than a predetermined threshold value and a mean value of intensity values of one or more pixels having intensity values that are equal to or greater than the threshold value and that are equal to or smaller than a maximum intensity value becomes a predetermined ratio, and setting the one or more pixels having the intensity values that are smaller than the threshold value, to a lower intensity region, and setting the one or more pixels having the intensity values that are equal to or greater than the threshold value and that are equal to or smaller than the maximum intensity value, to a higher intensity region.

The estimating of the boundary of the region of non-interest may include estimating a boundary in a shape of a straight line by using a mean value of the gradients of the X-ray image as a slope at a position of the X-ray image.

The estimating of the boundary of the region of non-interest may include estimating a boundary in a shape of a straight line at a position with a maximum gradient in the X-ray image.

The control method may further include removing unnecessary data from the binary-imaged X-ray image, before the calculating of the gradients of the binary-imaged X-ray image.

BRIEF DESCRIPTION OF THE DRAWINGS

The above and/or other aspects will become more apparent by describing certain exemplary embodiments with reference to the accompanying drawings, in which:

FIG. 7 is a flowchart illustrating a method of setting a region of non-interest, according to an exemplary embodiment;

FIGS. 9A, 9B, 9C, 9D, and 9E show a process of estimating a pectoral line from an X-ray image according to an exemplary embodiment;

DETAILED DESCRIPTION

Figure 1:
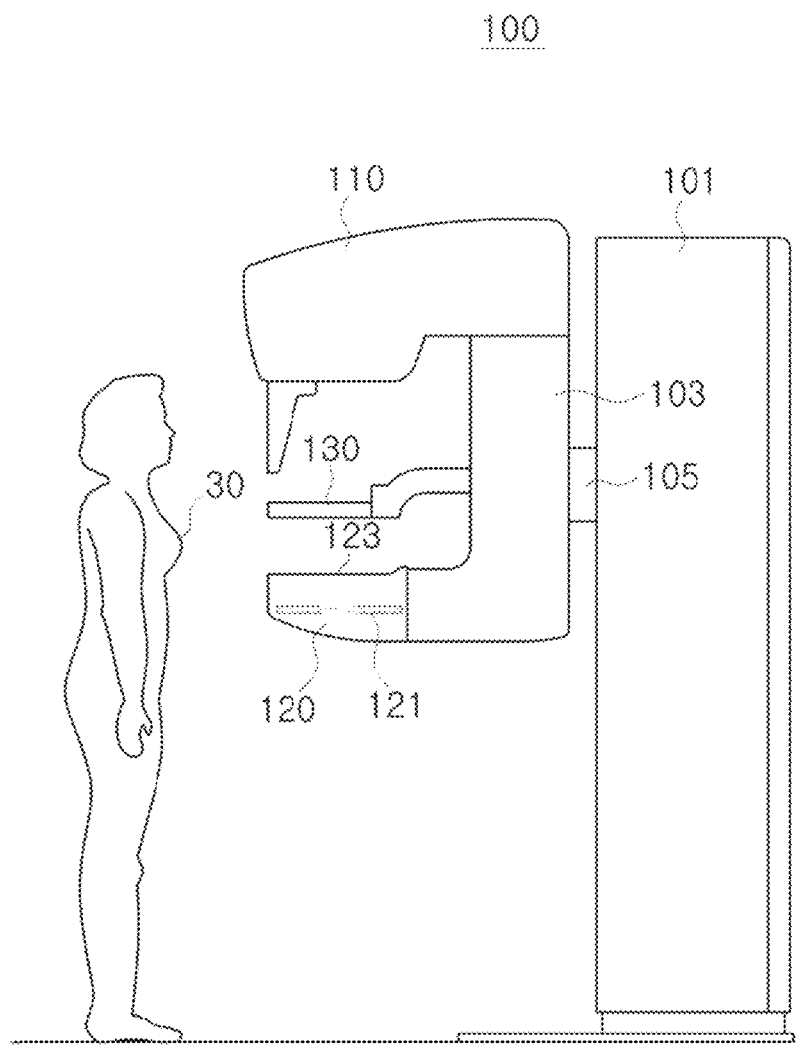
FIG. 1 is a view of an X-ray imaging apparatus according to an exemplary embodiment.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

Hereinafter, exemplary embodiments will be described in detail with reference to the appended drawings. In the following description, an X-ray imaging apparatus for mammography will be described as an example, however, an X-ray imaging apparatus according to exemplary embodiments is not limited to an X-ray imaging apparatus for mammography.

FIG. 1 is a view of an X-ray imaging apparatus according to an exemplary embodiment.

Referring to FIG. 1, an X-ray imaging apparatus 100 may include an X-ray source 110, an X-ray detection assembly 120, and a pressure paddle 130.

The X-ray source 110 and the X-ray detection assembly 120 may be connected to a frame 103 in such a manner that the X-ray source 110 and the X-ray detection assembly 120 face each other. The frame 103 may be connected to a main body 101 through an arm 105, and the arm 105 may move in an upward and/or downward direction to adjust the height of the frame 103 according to the height of an object. Also, the arm 105 may rotate at a predetermined angle so that the X-ray imaging apparatus 100 can acquire tomography images or three-dimensional (3D) images of the object 30.

The X-ray imaging apparatus 100 may be used to scan a breast and produce X-ray images about the breast. That is, the object 30 may be a breast. The object 30 may be a region to be diagnosed by the X-ray imaging apparatus 100, and the object may be a region of a living body including a human body.

Upon mammography, a breast which is the object 30 may be positioned between the X-ray source 110 and the X-ray detection assembly 120 so that X-rays transmitted through the breast among X-rays transmitted from the X-ray source 110 can be detected by the X-ray detection assembly 120.

The X-ray detection assembly 120 may function as a supporting panel or a table for supporting a breast. The X-ray detection assembly 120 is also called bucky. The X-ray detection assembly 120 may include an X-ray detector 121 to detect X-rays, and a breast contact part 123 that contacts a breast. The breast contact part 123 may be made of a material with excellent X-ray transmission, and for example, the breast contact part 123 may be implemented as a carbon sheet.

The X-ray imaging apparatus 100 for mammography may include a structural element that is different from those of general X-ray imaging apparatuses, according to tissue properties of a breast. One of such structural element is the pressure paddle 130 to press a breast, as shown in FIG. 1.

That is, if a breast is placed on the breast contact part 123 of the X-ray detection assembly 120, a user may manipulate an input unit 150 (see FIG. 4) to move the pressure paddle 130 in an upward and/or downward direction, to press the breast placed on the breast contact part 123. Herein, the "user" refers to a person who diagnoses the object 30 using the X-ray imaging apparatus 100, and may be a medical professional including a doctor, a radiologist, and a nurse. However, the user is not limited to a medical professional, and may be any person using the X-ray imaging apparatus 100.

After pressing the breast using the pressure paddle 130, the breast is scanned to acquire an X-ray image of the breast. It is desired that a clear X-ray image of the breast is acquired while reducing a dose of X-rays. To this end, an operation is performed, which will be described in more detail with reference to FIGS. 2 and 3, below.

Figure 2:
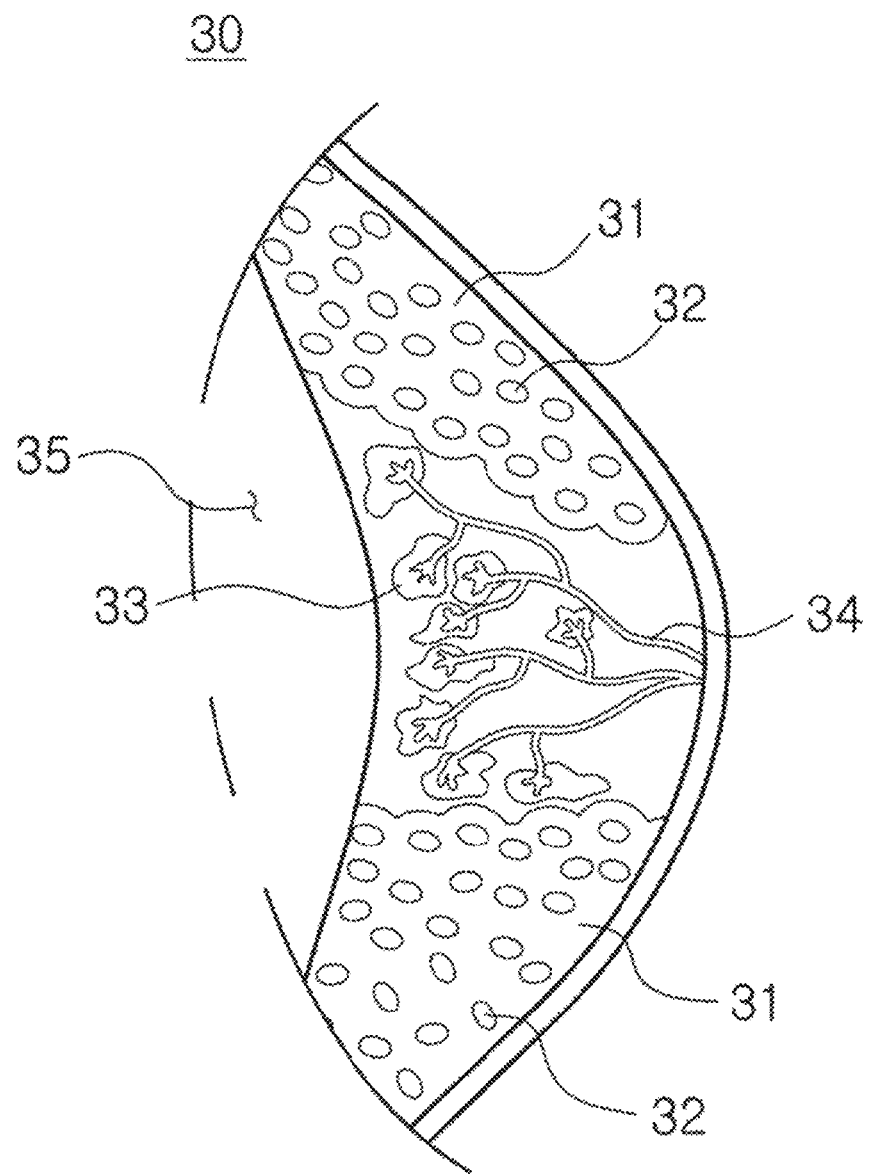
FIG. 2 illustrates an internal structure of a breast.

FIG. 2 illustrates an internal structure of a breast.

Referring to FIG. 2, the internal tissues of a breast 30 includes a fibrous tissue 31 surrounding the breast 30 and maintaining the shape of the breast 30, an adipose tissue 32 distributed over an entire region of the breast 30, a grandular tissue 33 which may produce breast milk, a duct tissue 34 that is a transfer duct of breast milk, a pectoral 35 to support the breast 30, etc. The tissues, such as the grandular tissue 33 and the duct tissue 34, which participate in producing and supplying breast milk among the above-mentioned tissue, are called fibroglandular tissues.

An attenuation coefficient is data representing a degree at which X-rays attenuate while being transmitted through a specific material. Since different internal materials included in an object have different attenuation coefficients, the internal structure of an object can be visualized based on a fact that different internal materials of the object have different attenuation coefficients.

Figure 3:
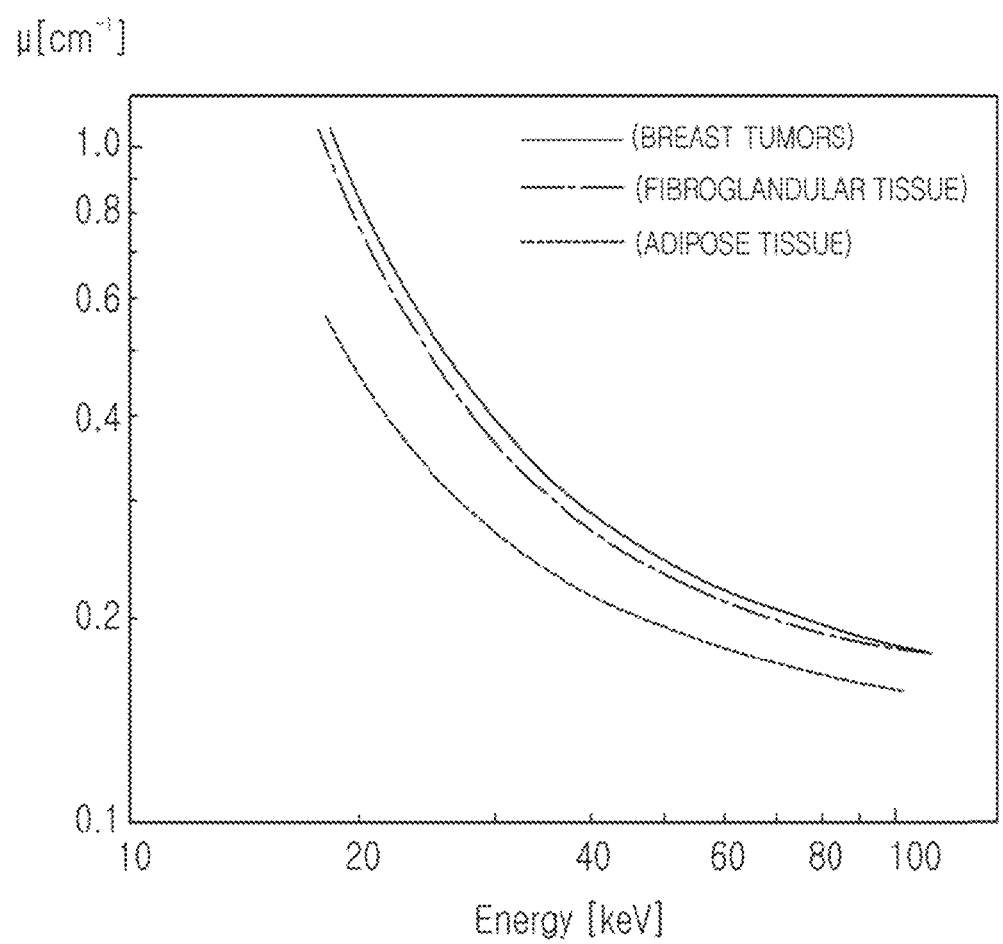
FIG. 3 is a graph showing a relationship between an energy band and an attenuation coefficient with respect to individual internal materials of a breast.

FIG. 3 is a graph showing a relationship between an energy band and an attenuation coefficient with respect to individual internal materials of a breast.

As shown in FIG. 3, attenuation coefficients of the internal materials of a breast do not show great differences among the internal materials of the breast. The reason is because the breast includes only soft tissues as illustrated in FIG. 2. Accordingly, in order to acquire a clear X-ray image, it is needed to thin the thickness of the breast by pressing the breast with the pressure paddle 130 (see FIG. 1). If the thickness of the breast is thinned, the internal materials of the breast may be spread out, without overlapping each other, in a direction in which X-rays are transmitted so that the quality of an X-ray image to be produced can be improved while reducing an amount of X-rays to be transmitted to the breast.

Referring again to FIG. 1, the pressure paddle 130 may be connected to the frame 103, which connects the X-ray source 110 to the X-ray detection assembly 120, in such a manner that the pressure paddle 130 is movable in an upward and/or downward direction. Upon mammography, the breast 30 is placed on the breast contact unit 123 of the X-ray detection assembly 120, and a user manipulates the input unit 150 (see FIG. 4) to move the pressure paddle 13 downwardly to press the breast 30. Next, X-rays are transmitted to the breast 30 in the state that the breast 30 is pressed, and the X-rays transmitted through the breast 30 are detected.

Hereinafter, respective components of the X-ray imaging apparatus 100 according to an exemplary embodiment will be described.

Figure 4:
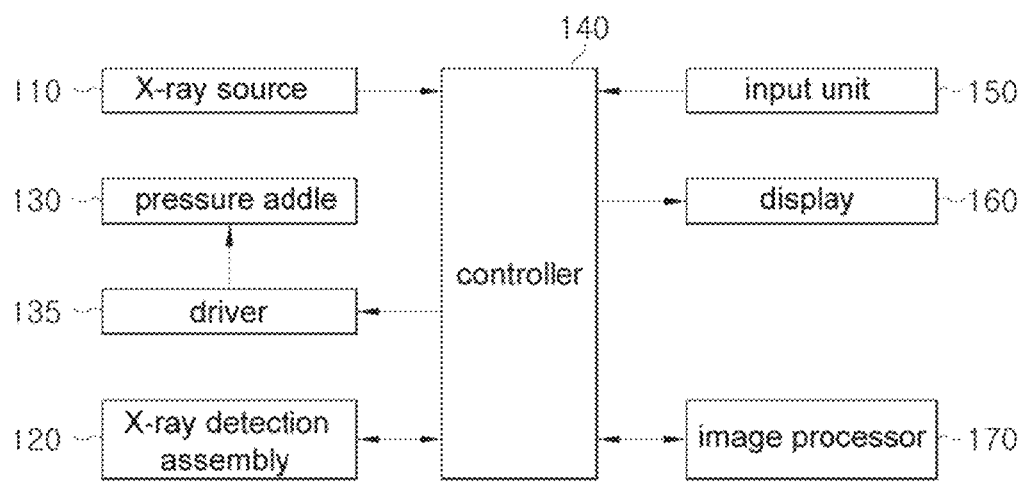
FIG. 4 is a block diagram of an X-ray imaging apparatus according to an exemplary embodiment.

FIG. 4 is a block diagram of the X-ray imaging apparatus 100 according to an exemplary embodiment.

Referring to FIG. 4, the X-ray imaging apparatus 100 may include the X-ray source 110, the X-ray detection assembly 120, the pressure paddle 130, a driver 135, a controller 140, the input unit 150, a display 160, and an image processor 170.

The X-ray source 110 may include an X-ray tube 111 to generate X-rays. The X-ray source 110 is also called an X-ray tube head or an X-ray tube assembly.

Figure 5:
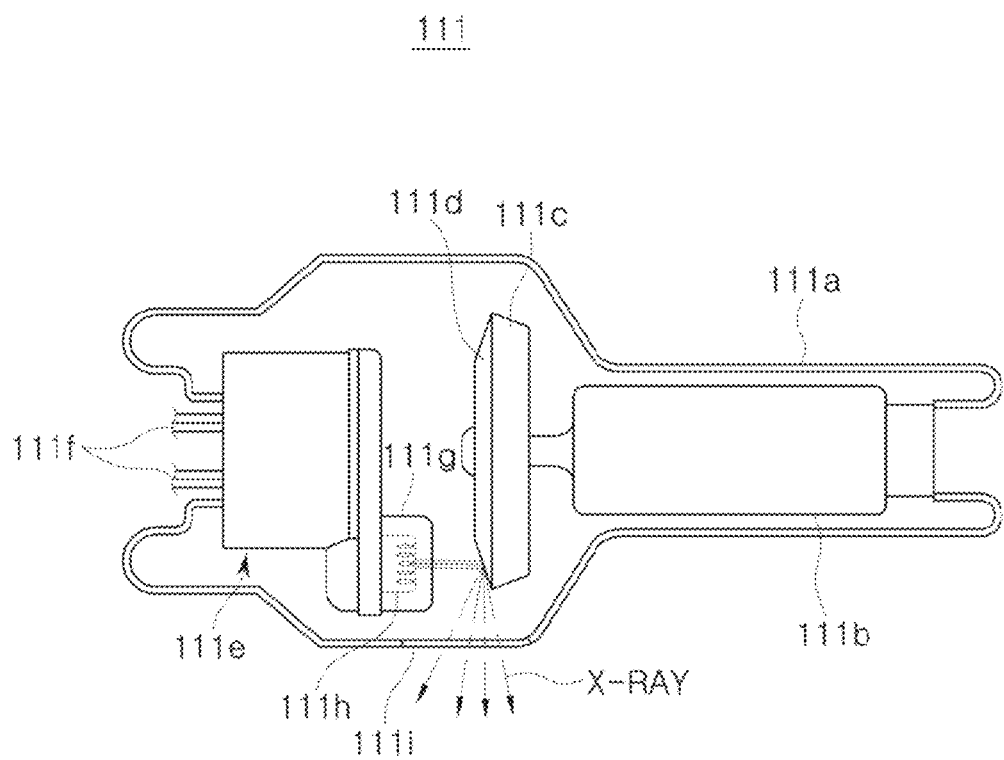
FIG. 5 illustrates an internal structure of an X-ray tube.

FIG. 5 illustrates an internal structure of the X-ray tube 111.

Referring to FIG. 5, the X-ray tube 111 may be embodied as a two-electrode vacuum tube including an anode 111c and a cathode 111e, and a body of the two-electrode vacuum tube may be a glass tube 111a including silica (or hard) glass or the like.

The cathode 111e includes a filament 111h and a focusing electrode 111g for focusing electrons, and the focusing electrode 111g is also called a focusing cup. The inside of a glass tube 111a is evacuated to a high vacuum state of about 10 mmHg, and the filament 111h of the cathode 111e is heated to a high temperature, thereby generating thermoelectrons. The filament 111h may be a tungsten filament, and the filament 111h may be heated by applying a current to electrical leads 111f connected to the filament 111h.

The anode 111c may include copper, and a target material 111d is applied on a surface of the anode 111c, the surface facing the cathode 111e, wherein the target material 111d may include a high-resistance material, e.g., Cr, Fe, Co, Ni, W, or Mo. The higher melting point the target material 111d has, the smaller the focal spot size is.

When a high voltage is applied between the cathode 111e and the anode 111c, thermoelectrons are accelerated and collide with the target material 111d of the anode 111e, thereby generating X-rays. The X-rays are transmitted to the outside through a window 111i. The window 111i may be a Beryllium (Be) thin film. Also, a filter (not shown) for filtering a specific energy band of X-rays may be provided on the front or rear side of the window 111i.

The target material 111d may be rotated by a rotor 111b. When the target material 111d rotates, the heat accumulation rate may increase about ten times per unit region and the focal spot size may be reduced, compared to when the target material 111d is fixed.

The voltage that is applied between the cathode 111e and the anode 111c of the X-ray tube 111 is called a tube voltage. The magnitude of a tube voltage may be expressed as a crest value (kVp). When the tube voltage increases, a velocity of thermoelectrons increases accordingly. Also, energy of X-rays (or energy of photons) that are generated when the thermoelectrons collide with the target material 111d increases. A current flowing through the X-ray tube 111 is called a tube current, and can be expressed as an average value (mA). When a tube current increases, the number of thermoelectrons emitted from the filament 111h increases, and as a result, a dose of X-rays (that is, the number of X-ray photons) that are generated when the thermoelectrons collide with the target material 111d increases.

Thus, energy of X-rays can be controlled by adjusting a tube voltage. Also, a dose or an intensity of X-rays can be controlled by adjusting a tube current and an X-ray exposure time. Accordingly, it is possible to control energy or an intensity of X-rays to be transmitted to an object, according to the type or properties of the object.

When X-rays to be transmitted have a predetermined energy band, the predetermined energy band may be defined by upper and lower limits. The upper limit of the predetermined energy band, that is, maximum energy of X-rays to be transmitted may be adjusted by the magnitude of a tube voltage, and the lower limit of the predetermined energy band, that is, minimum energy of X-rays to be transmitted may be adjusted by a filter. By filtering a low energy band of X-rays using the filter, average energy of X-rays to be transmitted may increase.

Although not shown in FIG. 5, the X-ray source 110 may further include a collimator in front of the window 111i. The collimator may function to adjust an irradiation range of X-rays that are transmitted from the X-ray tube 111, and to reduce scattering of X-rays.

If X-rays are transmitted from the X-ray source 110 to the object 30, X-rays transmitted through the object 30 may be detected by the X-ray detection assembly 120. The X-ray detection assembly 120 may include an X-ray detector 121 to detect X-rays.

Generally, the X-ray detector 121 can be classified according to a configuration of materials included in the X-ray detector 121, a method of converting detected X-rays into electrical signals, and a method of acquiring image signals.

The X-ray detector 121 may be classified into a mono type device or a hybrid type device according to a configuration of materials included in the X-ray detector 121.

If the X-ray detector 121 is a mono type device, at least a part of detecting X-rays and generating electrical signals, and at least a part of reading and processing the electrical signals may be performed by semiconductors including the same material, or may be performed by semiconductors manufactured by the same process. In this case, the X-ray detector 121 may include a light receiving device such as a charge coupled device (CCD) or a complementary metal oxide semiconductor (CMOS).

If the X-ray detector 121 is a hybrid type device, at least a part of detecting X-rays and generating electrical signals, and at least a part of reading and processing the electrical signals may be performed by semiconductors including different materials, or may be performed by semiconductors manufactured by different processes. For example, detecting X-rays may be performed by using a photodiode or a light receiving device such as CdZnTe, and reading and processing electrical signals may be performed by using a CMOS read out integrated circuit (CMOS ROIC), or detecting X-rays may be performed by using a strip detector, and reading and processing electrical signals may be performed by using an a-Si or a-Se flat panel system.

The X-ray detector 121 may use at least one of a direct conversion mode and an indirect conversion mode according to a method of converting X-rays into electrical signals.

In the direct conversion mode, if X-rays are transmitted, electron-hole pairs are temporarily generated in a light receiving device, electrons move to an anode and holes move to a cathode by an electric field applied to both terminals of the light receiving device. The X-ray detector 121 converts the movement of the electrons and holes into an electrical signal. The light receiving device may include a-Se, CdZnTe, $HgI_2$, or $PbI_2$.

In the indirect conversion mode, a scintillator is provided between a light receiving device and an X-ray source. If X-rays transmitted from an X-ray source react with the scintillator to emit photons having a wavelength of a visible light region, the light receiving device detects the photons, and converts the photons into an electrical signal. The light receiving device may include a-Si, and the scintillator may be a GADOX scintillator of a thin film type, or a CSI (Tl) of a micro pillar type or a needle type.

The X-ray detector 121 may use a charge integration mode of storing charges for a predetermined time period and acquiring a signal from the stored charges, or a photon counting mode of counting the number of photons having energy higher than threshold energy whenever a signal is generated by single X-ray photons, according to a method of acquiring image signals.

The X-ray detector 121 of the X-ray imaging apparatus 100 may be implemented using any one of the above-described various methods. However, exemplary embodiments are not limited to the above-described methods. That is, any other method of detecting X-rays, converting the X-rays into electrical signals, and acquiring image signals can be used.

For convenience of description, in an exemplary embodiment which will be described below, it is assumed that the X-ray detector 121 uses the direct conversion mode of acquiring electrical signals directly from X-rays, and the X-ray detector 121 is a hybrid type in which a light receiving device for detecting X-rays is integrated with a read-out circuit chip.

Figure 6:
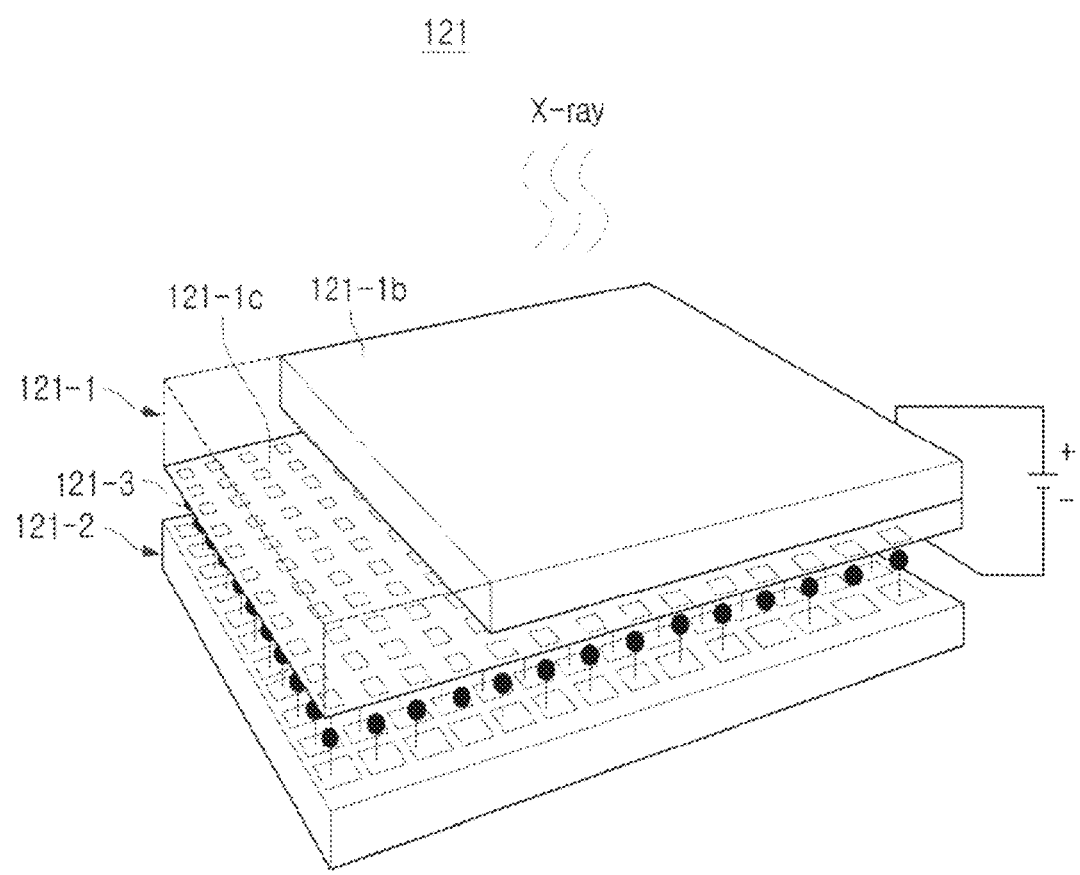
FIG. 6 illustrates a structure of an X-ray detector.

FIG. 6 illustrates a structure of the X-ray detector 121.

Referring to FIG. 6, the X-ray detector 121 may include a light receiving device 121-1 to detect X-rays and convert the X-rays into electrical signals, and a read-out circuit 121-2 to read out the electrical signals. The read-out circuit 121-2 may be in the form of a two-dimensional (2D) pixel array including a plurality of pixel areas. The light receiving device 121-1 may include a single crystal semiconductor material to ensure high resolution, high response speed, and a high dynamic region even under conditions of low energy and a small dose of X-rays. The single crystal semiconductor material may include Ge, CdTe, CdZnTe, or GaAs.

The light receiving device 121-1 may be in the form of a PIN photodiode. The PIN photodiode is fabricated by bonding a p-type layer 121-1*c* in which p-type semiconductors are arranged in the form of a 2D pixel array on the lower surface of an n-type semiconductor substrate 121-1*b* having high resistance. The read-out circuit 121-2, which is fabricated according to a CMOS process, is coupled with the light receiving device 121-1 in units of pixels. The CMOS read-out circuit 121-2 and the light receiving device 121-1 may be coupled by a flip-chip bonding (FCB) method. More specifically, the CMOS read-out circuit 121-2 and the light receiving device 121-1 may be coupled by forming bumps 121-3 with PbSn, In, or the like, reflowing, applying heat, and compressing. However, the X-ray detector 121 is not limited to this structure.

As not shown in FIG. 6, an X-ray grid to prevent X-rays from scattering may be provided in front of the X-ray detector 121.

When X-ray photons are incident to the light receiving device 121-1, electrons that have been in a valence band receive the energy of the photons so that total energy of the X-ray photons exceeds a bandgap energy difference to be excited to a conduction band. Accordingly, electron-hole pairs are created in a depletion region.

When metal electrodes are respectively formed on the p-type layer 121-1*c* and the n-type substrate 121-1*b* of the light receiving device 121-1, and a reversed bias voltage is applied between the p-type layer 121-1*c* and the n-type substrate 121-1*b*, the electrons in the electron-hole pairs created in the depletion region move to the n-type region, and the holes move to the p-type region. The holes moved to the p-type region are input to the read-out circuit 121-2 through the bumps 121-3 so that the read-out circuit 121-2 can read electrical signals generated by the photons. However, the electrons may be input to the read-out circuit 121-2 to generate electrical signals according to the structure of the light receiving device 121-1, an applied voltage, etc.

The read-out circuit 121-2 may have a 2D pixel array structure corresponding to the p-type semiconductors of the light receiving device 121-1, and read out an electrical signal in a unit of a pixel. If charges are input from the light receiving device 121-1 to the read-out circuit 121-2 through the bumps 123, the read-out circuit 121-2 outputs a voltage signal or an image signal that is represented by the number of photons, according to a circuit configuration of the read-out circuit 121-2.

The image signal output from the X-ray detector 121 is transferred to the image processor 170. The image processor 170 may analyze and process the image signal to produce an X-ray image of the breast. The X-ray image produced by the X-ray processor 170 may include a cranio-caudal (CC) image and a mediolateral oblique (MLO) image of a left or right side of the breast. However, the X-ray image produced by the X-ray processor 170 is not limited to these examples.

As described above, the pressure paddle 130 is used to thin the thickness of the breast 30 which is an object. To press the object 30, the pressure paddle 130 may be movable in an upward and/or downward direction. The thinning the thickness of the object 30 using the pressure paddle 130 has been described above, and a detailed description thereof will be omitted.

Referring again to FIG. 4, the driver 135 is used to move the pressure paddle 130 in the upward and/or downward direction, and in an exemplary embodiment, the driver 135 may be a motorized driver, a hydraulic driver, or a pneumatic driver, however, the driver 135 is not limited to these examples. In other words, if a control signal for moving the pressure paddle 130 is received from the controller 140 according to a user's command input through the input unit 150, the driver 135 may move the pressure paddle 130 upwardly or downwardly according to the control signal.

The input unit 150 is used to receive a command from a user. In an exemplary embodiment, the input unit 150 may be a mouse or a keyboard, however, the input unit 150 is not limited to these examples. Also, the input unit 150 may be integrated into the display 150, which will be described later, and may be implemented as a touch panel.

The display 160 may display an X-ray image processed by the image processor 170. Herein, the X-ray image may include an initial X-ray image, and an X-ray image from which a pectoral region has been removed, however, the X-ray image is not limited to these examples. The initial X-ray image and the X-ray image from which a pectoral region has been removed will be described in detail later.

The display 160 may be a liquid crystal display (LCD), a light emitting diode (LED) display, an organic light emitting diode (OLED) display, a plasma display panel (PDP), or a combination of one or more of the above-mentioned displays. However, the display 160 is not limited to these examples.

A user may check an initial X-ray image displayed on the display 160 with a user's naked eyes, and manipulate the input unit 150 to set a region of non-interest from the initial X-ray image.

The controller 140 controls overall operations of the X-ray imaging apparatus 100 so that components of the X-ray imaging apparatus 100 are connected to each other and operate with each other.

The controller 140 may include a processor, a read only memory (ROM) 112 that stores control programs for controlling the X-ray imaging apparatus 100, and a random access memory (RAM) 113 that temporarily stores signals and/or data received from the outside of the X-ray imaging apparatus 100 or is used as a workspace for various operations performed in the X-ray imaging apparatus 100. The processor may be implemented in the form of a system on chip (SoC) including a core and a graphic processing unit (GPU). The processor may be configured with a single-core, a dual-core, a triple-core, a quad-core, or a multiple core.

Also, the controller 140 may include a graphic processing board including a processor, a ROM, or a RAM on a separate circuit substrate electrically connected to the controller 140. The processor, ROM, and RAM may be connected to each other through internal buses.

Also, the controller 140 may be used to refer to a component including at least one of a processor, a ROM, and a RAM. Also, the controller 140 may be used to refer to a component including at least one of a processor, a ROM, a RAM, and a processing board.

The controller 140 may capture an X-ray image of an object according to pre-set mammography conditions. Herein, the mammography conditions may include the number of times of scanning, a scanning angle, a scanning location, a tube voltage, a tube current, a kind of a material configuring a filter, and a kind of a material configuring an anode. However, the mammography conditions are not limited to the above-mentioned conditions.

According to an exemplary embodiment, the controller 140 may set a region of non-interest from an initial X-ray image of an object. The region of non-interest may include a tissue of non-interest among the internal tissues of the object, a foreign material, and a surgical tool inserted into the object.

Herein, the tissue of non-interest may be a tissue having relatively low importance among the internal tissues of the object. For example, the tissue of non-interest may be a tissue such as a pectoral connected to a breast. That is, the tissue of non-interest can be understood as a tissue that does not need to be analyzed among the internal tissues of an object included in an X-ray image. The foreign material inserted in the object may be, for example, a prosthesis. The foreign material may be any material that does not belong to the original tissues of the object although the material is positioned inside the object.

In an exemplary embodiment, the region of non-interest may be set manually or automatically.

A method of manually setting a region of non-interest may be performed by a user by manipulating the input unit 150 to designate a block of a desired region in an X-ray image and setting the designated block to a region of non-interest. If the input unit 150 is a mouse, the user may check a region in which a non-interest target exists from an initial X-ray image displayed on the display 160, move the mouse to locate a mouse pointer in the corresponding region, and click and drag the mouse to designate a block of the corresponding region. Thus, a region of non-interest may be manually set by the user. However, this is only an example, and the user may set a region of non-interest in various ways according to a kind of the input unit 150.

A method of automatically setting a non-interest target includes setting a region of non-interest, based on mammography conditions of an initial X-ray image, the shapes and patterns of tissues, the intensity properties of tissues, information about changes in intensity between tissues, etc. Herein, the mammography conditions may correspond to mammography location information, however, the mammography conditions are not limited to this.

If the object is a breast and an object of non-interest is a pectoral in the breast, an initial X-ray image may include a right medio lateral oblique (RMLO) image, a left medio lateral oblique (LMLO) image, a right cranio caudal (RCC) image, and a left cranio caudal (LCC) image.

The controller 140 may analyze the shapes and patterns of tissues, and the intensity properties of the tissues in the X-ray image, compare the results of the analysis to those of the internal tissues of a reference breast to detect a region showing a difference as a non-interest target, and set a region of non-interest based on information about changes in intensity between the tissues.

For example, the controller 140 may detect a breast region from the initial X-ray image, determine a pectoral line in the shape of a straight line, and detect pectoral data using a gradation mask, thereby setting a region of non-interest.

The gradation mask may overlap the X-ray image. The gradation mask is a graphic mask in which shades, shapes, or textures gradually change. According to an exemplary embodiment, the controller 140 uses a mask in which shades change gradually, however, the controller 140 may use any other mask.

FIG. 7 is a flowchart illustrating a method of setting a region of non-interest, according to an exemplary embodiment.

A pectoral region for an LMLO image may include at least one of i) a region in the shape similar to a triangle that occupies an upper and left part of the initial X-ray image; ii) a region having a relatively higher intensity than the surrounding tissues; and iii) a region showing a relatively great change in intensity at the interface with the surrounding tissues.

Referring to FIG. 7, a method of setting a region of non-interest, according to an exemplary embodiment, will be described.

First, a controller may detect a breast region from an initial X-ray image, in operation S1100.

Figure 8A:
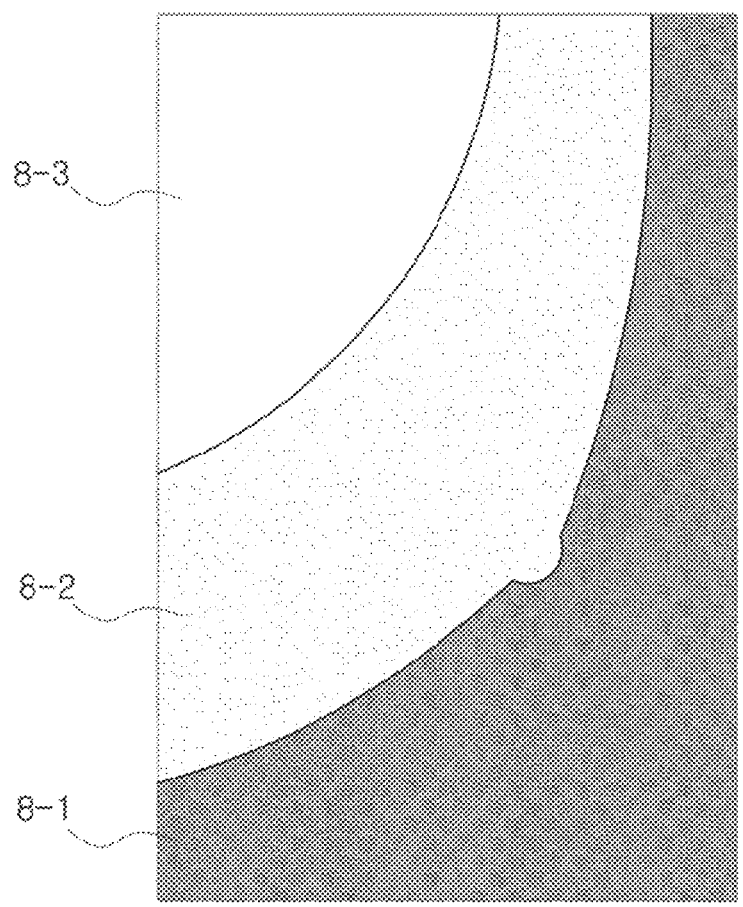
FIGS. 8A and 8B show an example of detecting breast regions in an initial X-ray image for a left medio lateral oblique (LMLO) image.
Figure 8B:
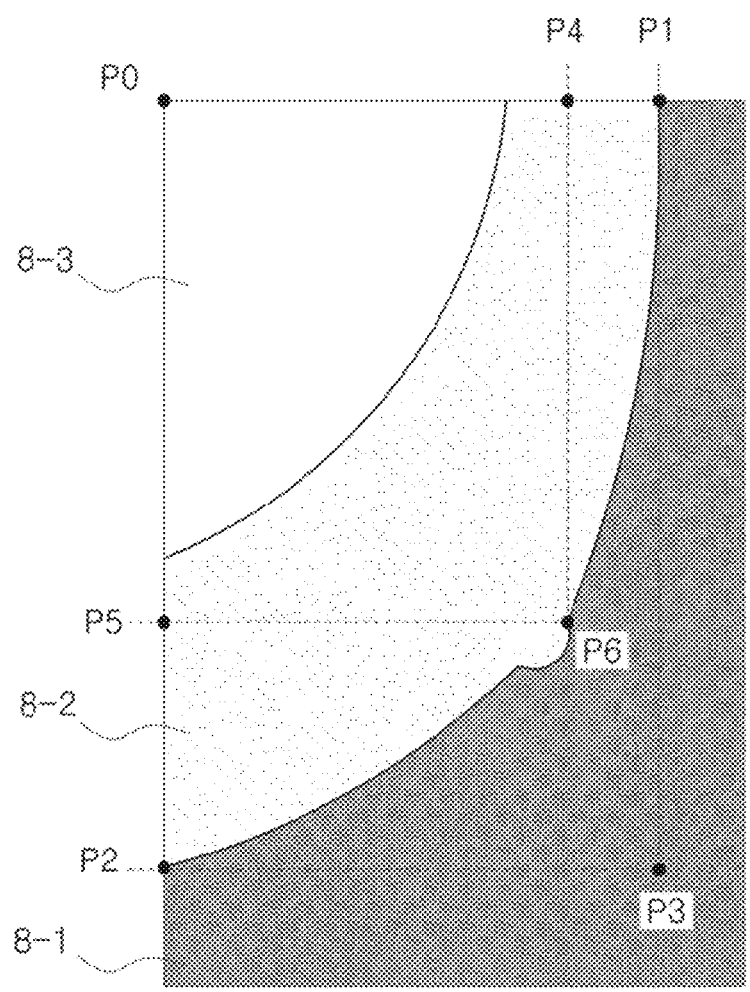

FIGS. 8A and 8B show an example of detecting breast regions in an initial X-ray image for an LMLO image.

Referring to FIG. 8A, the controller may detect breast regions 8-2 and 8-3 from a black background region 8-1.

For example, the controller may distinguish the breast regions 8-2 and 8-3 from the black background region 8-1, using a predetermined threshold value, based on an image histogram. The predetermined threshold value may be set by a user through an input unit, or may be preset when the corresponding X-ray imaging apparatus is manufactured. The image histogram is a graph showing a shade distribution of the X-ray image, and the image histogram may be created by an image processor and provided to the controller.

The controller may determine the predetermined threshold value based on the image histogram. For example, the controller may determine the predetermined threshold value such that a ratio between the number of pixels having intensity values that are smaller than the threshold value and the number of pixels having intensity values that are equal to or greater than the threshold value and equal to or smaller than a maximum intensity value becomes a predetermined ratio. The predetermined ratio may be set by a user through the input unit, or may be preset when the corresponding X-ray imaging apparatus is manufactured.

As another example, the controller may determine the predetermined threshold value such that a ratio between a mean value of intensity values of one or more pixels having intensity values that are smaller than the threshold value and a mean value of intensity values of one or more pixels having intensity values that are equal to or greater than the threshold value and equal to or smaller than a maximum intensity value becomes a predetermined ratio. The predetermined ratio may be set by a user through the input unit, or may be preset when the X-ray imaging apparatus is manufactured.

The mean value of the intensity values may include an arithmetic mean value, a geometric mean value, a harmonic mean value, and a median value of the pixel intensity values.

That is, the controller may determine pixels having intensity values that are smaller than the predetermined threshold value as the black background region 8-1, and determine pixels having intensity values that are equal to or greater than the predetermined threshold value and equal to or smaller than the maximum intensity value, as the breast regions 8-2 and 8-3, thereby detecting the breast regions 8-2 and 8-3.

Referring again to FIG. 7, the controller may estimate a pectoral line in the shape of a straight line, in operation S1200.

The controller may down-scale a resolution of the X-ray image in operation S1210 to improve processing speed, and reduce noise of the X-ray image in operation S1220. The down-scaled resolution of the X-ray image can be up-scaled after image processing.

To reduce noise of the initial X-ray image, the controller may use percentage normalization. The percentage normalization is a method of determining upper and lower limits of pixel levels for the initial X-ray image such that pixel levels approximate a normal distribution, and defining pixels having pixel levels within the upper and lower limits as valid data.

Also, to reduce noise of the initial X-ray image, the controller may perform blurring on the initial X-ray image, wherein the blurring may be performed through a frequency domain convolution or a spatial domain convolution using a Gaussian mask.

The controller may set a region of interest to clearly detect the pectoral region, in operation S1230.

For example, referring to FIG. 8B, to set a final region of interest that is defined by points P0', P4', P5', and P6' (shown in FIG. 9A), from an initial region of interest that is defined by points P0, P1, P2, and P3, the controller may set a higher intensity region and a lower intensity region of an intermediate region of interest that is defined by points P0, P4, P5, and P6, based on intensity values.

For example, the initial region of interest that is defined by the points P0, P1, P2, and P3 may be arbitrarily set by an input from a user. Alternatively, the controller may set a rightmost point of the breast regions 8-2 and 8-3 to the point P1, and a lowermost point of the breast regions 8-2 and 8-3 to the point P2, thereby setting an initial region of interest, which is defined by points P0, P1, P2, and P3, in the shape of a rectangle. If the X-ray image is an RMLO image or an RCC image, the controller may set a leftmost point of the breast regions 8-2 and 8-3 of the RMLO image or the RCC image to the point P1, and a lowermost point of the breast regions 8-2 and 8-3 to P2 of the RMLO image or the RCC image. That is, the initial region of interest defined by the points P0, P1, P2, and P3 may be set according to the locations of the breast regions 8-2 and 8-3 in the image or according to a user or a manufacturer.

Next, the controller may set a midpoint or a predetermined point P5 on a line connecting the points P0 and P2, and a midpoint or a predetermined point P4 on a line connecting the points P0 and P1, thereby setting an intermediate region of interest in the shape of a rectangle, which is defined by the points P0, P4, P5, and P6. Next, the controller may divide the intermediate region of interest defined by the points P0, P4, P5, and P6 into a higher intensity region and a lower intensity region, based on intensity values.

The controller may use an image histogram to divide the intermediate region of interest defined by the points P0, P4, P5, and P6 into a higher intensity region and a lower intensity region. For example, the controller may adjust the points P4 and P5 such that a ratio between a mean value of intensity values of one or more pixels having intensity values that are smaller than a threshold value and a mean value of intensity values of one or more pixels having intensity values that are equal to or greater than the threshold value and equal to or smaller than a maximum intensity value becomes a predetermined ratio, thereby setting the final region of interest defined by the points P0, P4', P5', and P6. Herein, the predetermined ratio may be 2:1, or the predetermined ratio may be arbitrarily set by a user or a manufacturer.

The threshold value may be arbitrarily set by a user, or may be preset when the X-ray imaging apparatus is manufactured. Also, the controller may automatically determine the threshold value, and the controller may use an image histogram to determine the threshold value. The threshold value is used as a criterion to divide a region into a higher intensity region (one or more pixels having intensity values that are equal to or greater than the threshold value and equal to or smaller than a maximum intensity value) and a lower intensity region (one or more pixels having intensity values that are smaller than the threshold value).

That is, the controller may adjust the points P4 and P5 such that a ratio between a mean value of intensity values of a higher intensity region having intensity values that are smaller than the threshold value and a mean value of intensity values of a lower intensity region having intensity values that are equal to or greater than the threshold value and equal to or smaller than a maximum intensity value becomes a predetermined ratio, thereby setting the final region of interest defined by the points P0, P4', P5', and P6.

The mean value of the intensity values may include an arithmetic mean value, a geometric mean value, a harmonic mean value, and a median value of the pixel intensity values.

In operation S1240, the controller may remove undesired data from the final region of interest by performing binary imaging and morphological processing on the final region of interest defined by the points P0, P4', P5', and P6. The morphological processing will be described later.

Figure 9A:
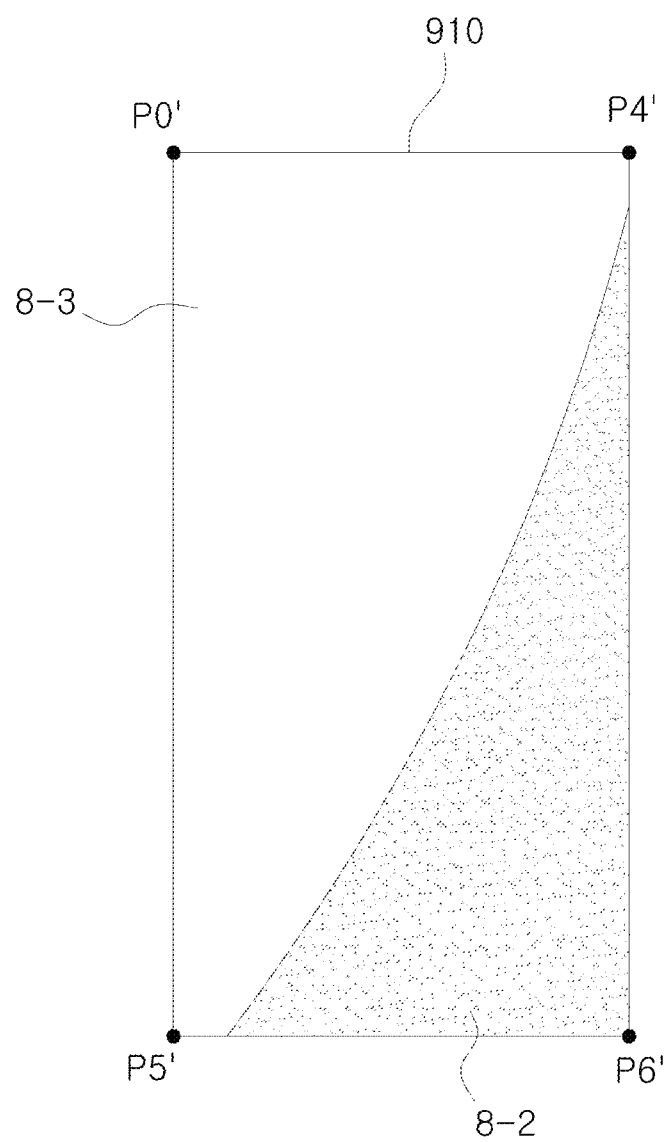
Figure 9C:
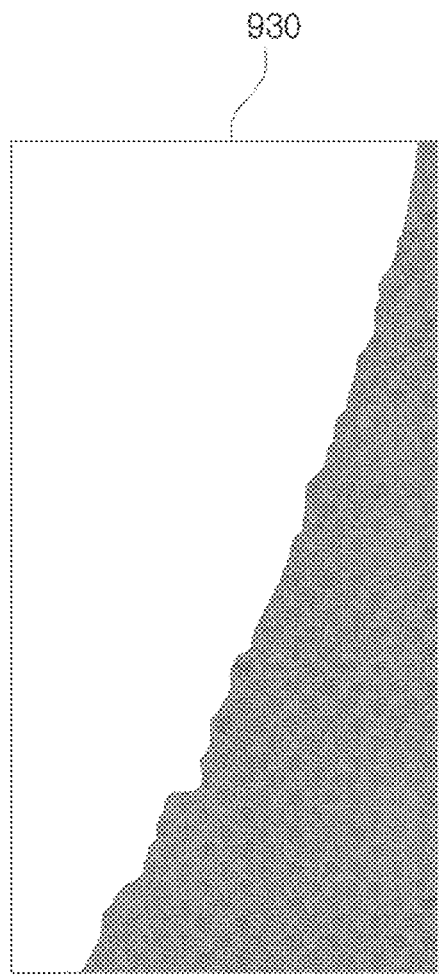
Figure 9D:
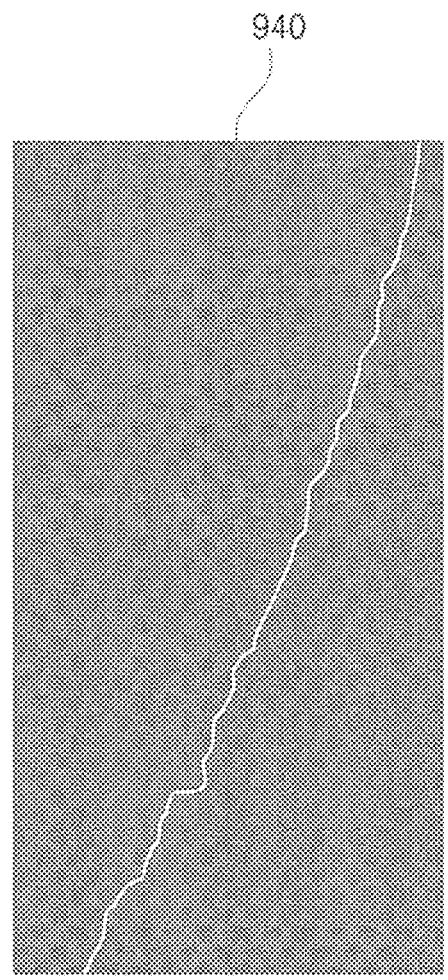
Figure 9E:
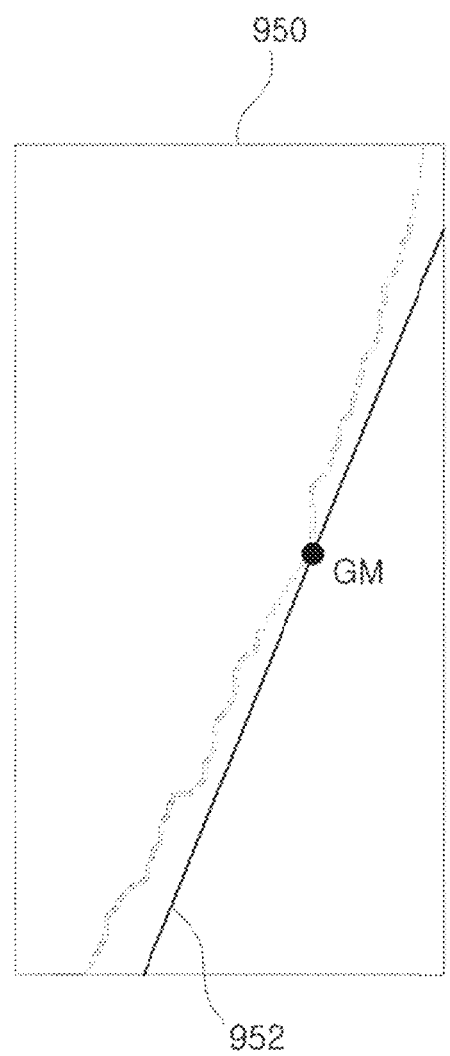

FIGS. 9A, 9B, 9C, 9D, and 9E show a process of estimating a pectoral line from an X-ray image according to an exemplary embodiment. In an exemplary embodiment, an X-ray image 910 of the final region of interest is obtained, as shown in FIG. 9A, and binary imaging is performed on the X-ray image 910 of the final region of interest to obtain a binary X-ray image 920, as shown in FIG. 9B. Next, morphological processing is performed on the binary X-ray image 920 to obtain a morphological-processed X-ray image 930, as shown in FIG. 9C, and pectoral lines are estimated from the morphological-processed X-ray image 930, as shown in FIGS. 9D and 9E.

In detail, the controller may distinguish the higher intensity region from the lower intensity region, perform binary imaging to produce the binary X-ray image 920 as shown in FIG. 9B, and apply dilation and erosion operations which are a kind of morphological processing to the binary X-ray image 920 to remove undesired data from the binary X-ray image 920 and thus produce a morphological-processed X-ray image 930, as shown in FIG. 9C. The controller may correct a boundary and remove undesired data such as a hole 9-1 through the morphological processing.

Next, the controller may estimate a pectoral line in the shape of a straight line, in operation S1250. To estimate a pectoral line in the shape of a straight line, the controller may calculate gradients for the boundary of the higher intensity region and the lower intensity region. For example, the controller may calculate non-positive gradients.

Figure 10:
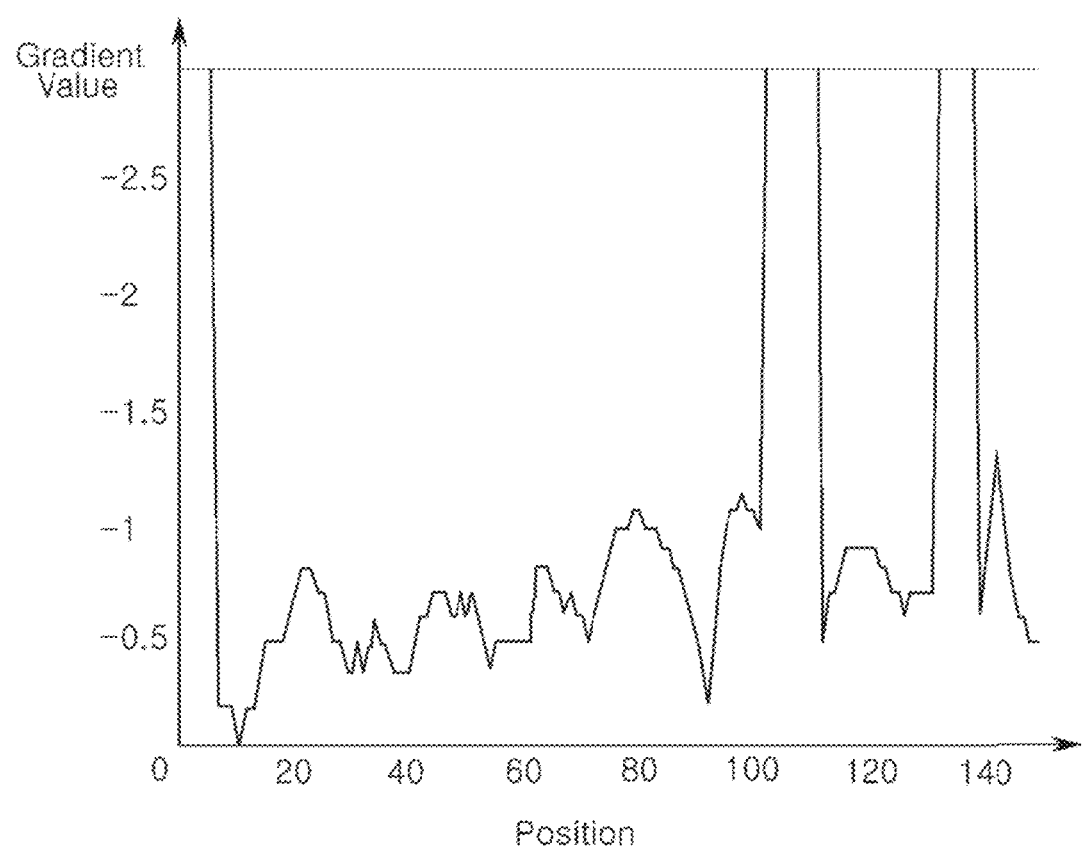
FIG. 10 is a graph showing a gradient according to a position in an X-ray image.

FIG. 9D shows an image 940 acquired by calculating gradients for the morphological-processed X-ray image 930 of FIG. 9C, FIG. 9E shows an image 950 including an estimated pectoral line 952 in the shape of a straight line, and FIG. 10 is a graph showing a gradient according to a position in the morphological-processed X-ray image 930 of FIG. 9C.

As shown in FIG. 9E, the controller may estimate the pectoral line 952 in the shape of a straight line having a gradient determined based on a mean value of the calculated gradients at a position GM having a maximum gradient. The mean value of the calculated gradients may include an arithmetic mean value, a geometric mean value, a harmonic mean value, and a median value of the gradients.

Next, the controller may detect pectoral data using a gradation mask, in operation 1300.

FIGS. 11A, 11B, 11C, and 11D are views for describing an example of detecting the pectoral data in the LMLO image according to an exemplary embodiment.

Figure 11A:
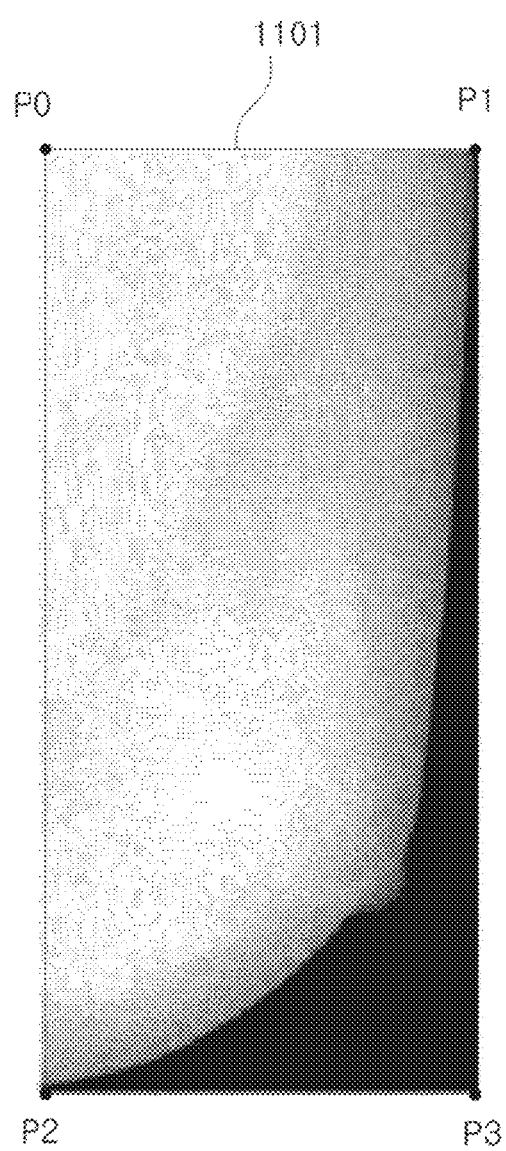
FIGS. 11A, 11B, 11C, and 11D are views for describing an example of a process of detecting pectoral data according to an exemplary embodiment.
Figure 11B:
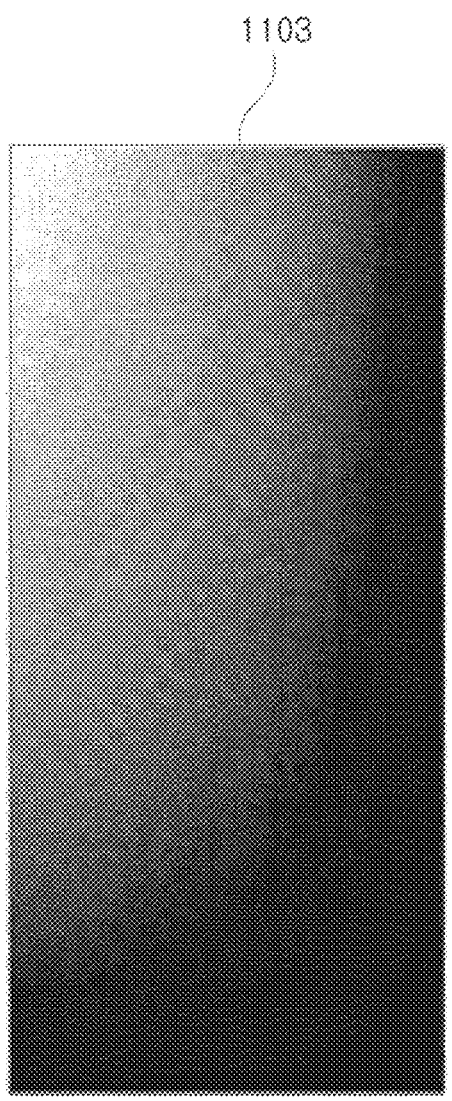
Figure 11C:
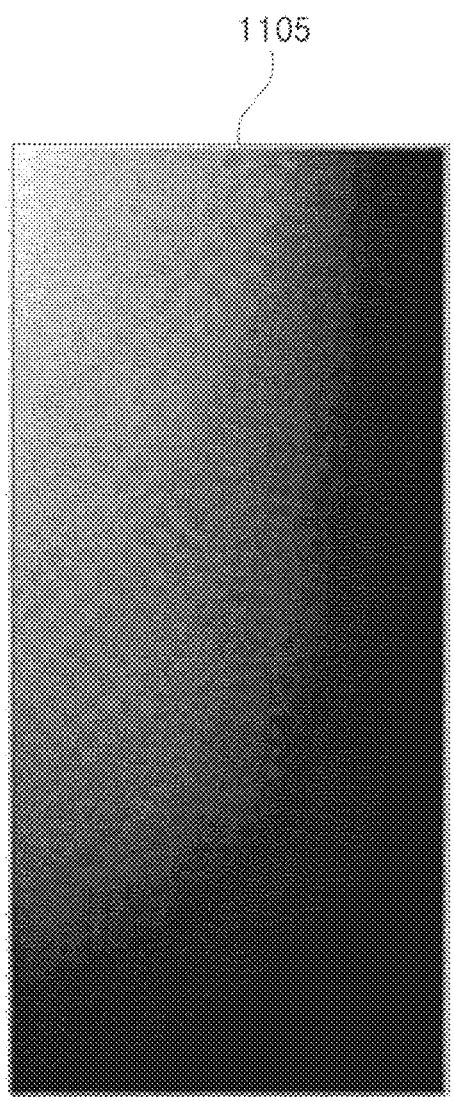
Figure 11D:
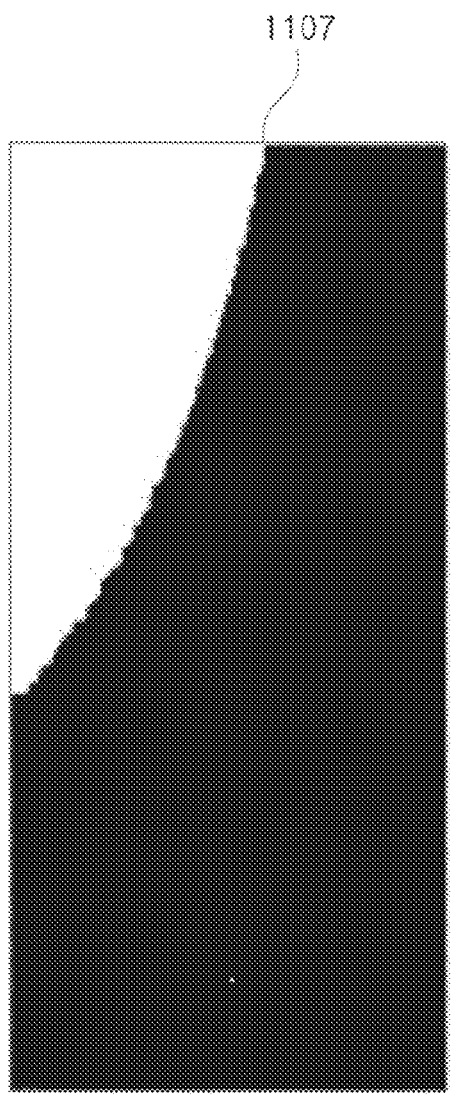

FIG. 11A shows an X-ray image 1101 corresponding to the initial region of interest defined by the points P0, P1, P2, and P3 of the X-ray image, FIG. 11B shows a representation 1103 of the gradation mask, FIG. 11C shows a resultant image 1105 acquired by multiplying the X-ray image 1101 by the gradation mask, and FIG. 11D shows an image 1107 including the pectoral data detected by the controller.

The controller may create the gradation mask having the same size as the initial region of interest defined by the points P0, P1, P2, and P3, wherein the gradation mask is created with a pattern in which intensity is reduced in a direction from an upper, left part to a lower, right part of the gradation mask. However, if the X-ray image is an RMLO image or an RCC image, the gradation mask may be created with a pattern in which intensity is reduced from an upper, right part to a lower, left part of the gradation mask.

If the controller applies the gradation mask to the X-ray image 1101, a pectoral line 952 may be estimated as shown in FIG. 9E, and the controller may detect pectoral data by using an intensity value of a position GM with a maximum gradient as a threshold value.

For example, the controller may allocate a value of "0" to pixels having intensity values that are smaller than the threshold value, and a value of "1" to pixels having intensity values that are equal to or greater than the threshold value and equal to or smaller than a maximum intensity value, using an image histogram, to perform binary imaging on the image 1105, and may detect a region of the pixels to which the value of "1" has been allocated, as a pectoral data region.

Next, the controller may produce an X-ray image from which a pectoral region has been removed, based on the estimated pectoral line in the shape of the straight line and the detected pectoral data, in operation S1400.

In detail, the controller may up-scale the resolution of the X-ray image to reconstruct the X-ray image, and detect the breast region 8-2 from which the pectoral region 8-3 has been removed, based on the detected breast regions 8-2 and 8-3 and the detected pectoral region 8-3. The pectoral region 8-3 may be determined as a region in which an upper, left region extracted by using, as a boundary, the pectoral line in the shape of the straight line which overlaps the pectoral data region detected using the gradation mask. However, if the X-ray image is an RMLO image or an RCC image, the pectoral region 8-3 may be determined as a region in which an upper, right region extracted by using, as a boundary, the pectoral line in the shape of the straight line which overlaps the pectoral data region detected using the gradation mask.

If two or more non-interest targets (for example, pectorals and a prosthesis) exist in the X-ray image, the controller may analyze the shapes and patterns of tissues, and the intensity properties of the tissues in the X-ray image, compare the results of the analysis to those of the internal tissues of a reference breast to detect regions showing differences based on a result of comparison as objects of non-interest, and set regions of non-interest based on information about changes in intensity between the tissues.

A method of automatically setting a region of non-interest has been described above, however, the method as described above is given only as an example.

Also, information about a location at which the region of non-interest set by the method as described above is positioned in the X-ray image may be stored in a storage unit (not shown).

Although not shown in FIG. 4, the X-ray imaging apparatus 100 according to an exemplary embodiment may further include a storage unit (not shown) to store data as described above, that is, mammography conditions for the properties of tissues, information about a location at which a region of non-interest that is manually or automatically set is positioned in an X-ray image, etc. The storage unit may be implemented as storage medium, such as a read only memory (ROM), a random access memory (RAM), a programmable read only memory (PROM), an erasable programmable read only memory (EPROM), a non-volatile memory device such as a flash memory, a volatile memory device such as a RAM, a hard disc, and an optical disc. However, the storage unit is not limited to the above-mentioned devices, and may be implemented as any other storage device well-known to one of ordinary skill in the art.

The image processor 170 may read out electrical signals from the X-ray detection assembly 120 to acquire image signals, and perform signal processing on the image signals to produce an X-ray image.

More specifically, the image processor 170 may process electrical signals read out from the X-ray detection assembly 120 to produce an initial X-ray image.

Also, the image processor 170 may create an image histogram of the X-ray image, and provide the image histogram to the controller 140. The initial X-ray image may be provided to the display 160 and displayed on the display 160.

Exemplary embodiments have been described above. A final X-ray image from which a region of non-interest has been removed, produced according to the exemplary embodiments, can be used as input information for computer-aided diagnosis (CAD), and/or can be used by medical professionals to determine and diagnose lesions in breasts.

Some of the components which constitute the X-ray imaging apparatus according to the exemplary embodiments as described above may be implemented by modules. The term "module" means a software or hardware component such as a field programmable gate array (FPGA) or an application specific integrated circuit (ASIC) and the modules each perform assigned functions. However, the modules are not limited to software or hardware. The modules may be configured in an addressable storage medium, or may be configured to run on at least one processor.

Examples of the modules may include components such as software components, object-oriented software components, class components, and task components; processors, functions, attributes, procedures, sub-routines, segments of program codes, drivers, firmware, microcodes, circuits, data, databases, data structures, tables, arrays, and variables. The functions provided by the components and the modules may be combined into fewer components and/or modules may be separated into additional components and modules. In addition, the components and modules may execute one or more central processing units (CPUs) in a device.

In addition to the above-described exemplary embodiments, the exemplary embodiments may be realized through medium including a computer-readable code and/or instruction to control at least one processing element of the above-described embodiments, for example, a computer readable medium. The medium may correspond to a medium and/or media that enable storage and/or transmission of the computer-readable code.

The computer-readable code may also be recorded in the medium and transmitted via the Internet. The medium, for example, may include a recording medium, such as a magnetic storage medium (e.g., a ROM, floppy disc, and hard disk) and an optical recording medium (e.g., a compact disc (CD)-ROM or a digital versatile disc (DVD)), and a transmission medium such as carrier waves. According to the exemplary embodiments, the medium may be a signal, such as a complex signal or bitstream. The medium may further include a distributed network, and therefore the computer-readable code may be stored, transmitted, and executed in a distributed manner. Moreover, the processing element may include a processor or computer processor by way of example. The processing element may be distributed and/or included in a single device.

According to the X-ray imaging apparatus and the control method for the same according to the exemplary embodiments, by setting a region of non-interest in an X-ray image with high accuracy, an X-ray image from which a region of non-interest has been removed can be produced.

The foregoing exemplary embodiments and advantages are merely exemplary and are not to be construed as limiting. The present teaching can be readily applied to other types of apparatuses. The description of the exemplary embodiments is intended to be illustrative, and not to limit the scope of the claims, and many alternatives, modifications, and variations will be apparent to those skilled in the art.

What is claimed is:

1. An X-ray imaging apparatus comprising:
   an X-ray source configured to transmit X-rays;
   an X-ray detection assembly configured to detect the X-rays, and to convert the detected X-rays into an electrical signal;
   a controller configured to process an X-ray image generated based on the electric signal by changing shades of the X-ray image, and set a region of non-interest of the X-ray image based on the X-ray image and the processed X-ray image,
   wherein the controller is configured to perform, based on a threshold value, binary imaging on the processed X-ray image having the changed shades, and set a higher intensity region of the processed X-ray image as the region of non-interest in the X-ray image, and
   wherein the threshold value corresponds to an intensity value of a position having a maximum gradient in the X-ray image.

2. The X-ray imaging apparatus according to claim 1, wherein the controller is configured to set the region of non-interest using a gradation mask.

3. The X-ray imaging apparatus according to claim 1, wherein the region of non-interest is a region corresponding to a pectoral region.

4. The X-ray imaging apparatus according to claim 1, wherein the controller is configured to process the X-ray image by multiplying the X-ray image by a shading mask having a pattern in which intensity is gradually reduced in a certain direction in the pattern.

5. The X-ray imaging apparatus according to claim 1, wherein
the controller is configured to perform binary imaging on the X-ray image based on an image histogram of the X-ray image, and calculate gradients of the binary-imaged X-ray image to estimate a boundary of the region of non-interest.

6. The X-ray imaging apparatus according to claim 5, wherein the controller is configured to determine a predetermined threshold value such that a ratio between a mean value of intensity values of pixels having intensity values that are smaller than the predetermined threshold value and a mean value of intensity values of pixels having intensity values that are equal to or greater than the predetermined threshold value and equal to or smaller than a maximum intensity value becomes a predetermined ratio, and perform the binary imaging on the X-ray image by setting a lower intensity region based on the pixels having the intensity values that are smaller than the predetermined threshold value and setting a higher intensity region based on the pixels having the intensity values that are equal to or greater than the predetermined threshold value and equal to or smaller than the maximum intensity value.

7. The X-ray imaging apparatus according to claim 5, wherein the controller is configured to estimate a boundary of the region of non-interest as a straight line having a gradient determined based on a mean value of the gradients of the X-ray image.

8. The X-ray imaging apparatus according to claim 5, wherein the controller is configured to estimate a boundary of the region of non-interest in a shape of a straight line at the position having the maximum gradient in the X-ray image.

9. The X-ray imaging apparatus according to claim 5, wherein the controller is configured to remove non-interest data from the binary-imaged X-ray image.

10. The X-ray imaging apparatus according to claim 1, wherein the controller is configured to:
perform binary imaging on the processed X-ray image to set a first region based on the binary-imaged processed X-ray image;
perform binary imaging on the X-ray image and calculate the gradients of the binary-imaged X-ray image to set a second region based on the calculated gradient; and
set the region of non-interest based on an overlapping area between the first region and the second region.

11. A control method of an X-ray imaging apparatus, the control method comprising:
processing, by a controller an X-ray image by changing shades of the X-ray image and setting a region of non-interest in the X-ray image based on the X-ray image and the processed X-ray image; and
removing, by the controller, the region of non-interest from the X-ray image,
wherein the setting the region of non-interest further comprises performing, based on a threshold value, binary imaging on the processed X-ray image having the changed shades to set a higher intensity region of the X-ray image as the region of non-interest, and
wherein the threshold value corresponds to an intensity value of a position having a maximum gradient in the X-ray image.

12. The control method according to claim 11, wherein the setting the region of non-interest comprises setting the region of non-interest using a gradation mask.

13. The control method according to claim 11, wherein the setting the region of non-interest comprises:
generating the processed X-ray image by multiplying the X-ray image by a shading mask having a pattern in which intensity is gradually reduced in a predetermined direction in the pattern.

14. The control method according to claim 11, wherein the setting the region of non-interest comprises:
performing binary imaging on the X-ray image based on an image histogram;
calculating gradients of the binary-imaged X-ray image; and
estimating a boundary of the region of non-interest using the gradients of the X-ray image.

15. The control method according to claim 14, wherein the performing the binary imaging on the X-ray image comprises:
setting a predetermined threshold value such that a ratio between a mean value of intensity values of pixels having intensity values that are smaller than the predetermined threshold value and a mean value of intensity values of pixels having intensity values that are equal to or greater than the predetermined threshold value and equal to or smaller than a maximum intensity value becomes a predetermined ratio,
setting a lower intensity region based on the pixels having the intensity values that are smaller than the predetermined threshold value, and
setting a higher intensity region based on the pixels having the intensity values that are equal to or greater than the predetermined threshold value and equal to or smaller than the maximum intensity value.

16. The control method according to claim 14, wherein the estimating the boundary of the region of non-interest comprises:
estimating the boundary of the region of non-interest as a straight line having a gradient determined based on a mean value of the gradients of the X-ray image at a position of the X-ray image.

17. The control method according to claim 14, wherein the estimating the boundary of the region of non-interest comprises:
estimating a boundary of the region of non-interest as a straight line at the position having the maximum gradient in the X-ray image.

18. The control method according to claim 14, further comprising:
removing, by the controller, non-interest data from the binary-imaged X-ray image prior to the calculating the gradients of the binary-imaged X-ray image.

* * * * *